United States Patent
Ebisawa

(10) Patent No.: US 10,417,782 B2
(45) Date of Patent: Sep. 17, 2019

(54) CORNEAL REFLECTION POSITION ESTIMATION SYSTEM, CORNEAL REFLECTION POSITION ESTIMATION METHOD, CORNEAL REFLECTION POSITION ESTIMATION PROGRAM, PUPIL DETECTION SYSTEM, PUPIL DETECTION METHOD, PUPIL DETECTION PROGRAM, GAZE DETECTION SYSTEM, GAZE DETECTION METHOD, GAZE DETECTION PROGRAM, FACE ORIENTATION DETECTION SYSTEM, FACE ORIENTATION DETECTION METHOD, AND FACE ORIENTATION DETECTION PROGRAM

(71) Applicant: NATIONAL UNIVERSITY CORPORATION SHIZUOKA UNIVERSITY, Shizuoka-shi, Shizuoka (JP)

(72) Inventor: Yoshinobu Ebisawa, Hamamatsu (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 39 days.

(21) Appl. No.: 15/505,781

(22) PCT Filed: Jul. 27, 2015

(86) PCT No.: PCT/JP2015/071270
§ 371 (c)(1),
(2) Date: Feb. 22, 2017

(87) PCT Pub. No.: WO2016/027627
PCT Pub. Date: Feb. 25, 2016

(65) Prior Publication Data
US 2017/0278269 A1  Sep. 28, 2017

(30) Foreign Application Priority Data

Aug. 22, 2014  (JP) .................................. 2014-169508

(51) Int. Cl.
*G06K 9/00* (2006.01)
*G06T 7/73* (2017.01)
(Continued)

(52) U.S. Cl.
CPC ................ *G06T 7/74* (2017.01); *A61B 3/113* (2013.01); *G06K 9/00248* (2013.01);
(Continued)

(58) Field of Classification Search
CPC ............ G06K 9/00248; G06K 9/00604; G06T 2207/10152; G06T 2207/20224;
(Continued)

(56) References Cited

U.S. PATENT DOCUMENTS

| | | | | |
|---|---|---|---|---|
| 2011/0242486 A1* | 10/2011 | Ebisawa | ................ | G06F 3/013 351/206 |
| 2013/0188834 A1* | 7/2013 | Ebisawa | ................ | A61B 3/113 382/103 |
| 2013/0329957 A1* | 12/2013 | Ebisawa | ................ | A61B 3/113 382/103 |

FOREIGN PATENT DOCUMENTS

| | | |
|---|---|---|
| EP | 2 649 932 A1 | 10/2013 |
| JP | 2005-185431 | 7/2005 |

(Continued)

OTHER PUBLICATIONS

Notification of Transmittal of Translation of the International Preliminary Report on Patentability (Chapter I or Chapter II) for PCT/JP2015/071270 dated Mar. 7, 2017.
(Continued)

*Primary Examiner* — Avinash Yentrapati
(74) *Attorney, Agent, or Firm* — Ostrolenk Faber LLP

(57) ABSTRACT

A corneal reflection position estimation system according to an embodiment includes: an image acquisition unit config-
(Continued)

ured to continuously acquire an image of an eye of a subject by controlling a camera equipped with a light source, the image acquisition unit being configured to acquire a plurality of pupil images taken by using light from the light source and then acquire one unilluminated image taken without using light from the light source; and an estimation unit configured to calculate positions of corneal reflection or corneal sphere centers, which correspond to the plurality of pupil images, as reference positions, calculate a movement vector of the corneal reflection or the corneal sphere center based on a plurality of the reference positions, and estimate the corneal reflection position in the unilluminated image based on at least the movement vector.

13 Claims, 12 Drawing Sheets

(51) Int. Cl.
    *A61B 3/113*     (2006.01)
    *G06T 7/254*     (2017.01)
    *G06T 7/277*     (2017.01)
    *G06T 7/70*     (2017.01)

(52) U.S. Cl.
    CPC ..... *G06K 9/00255* (2013.01); *G06K 9/00604* (2013.01); *G06T 7/254* (2017.01); *G06T 7/277* (2017.01); *G06T 7/70* (2017.01); *G06T 2207/10021* (2013.01); *G06T 2207/10152* (2013.01); *G06T 2207/20224* (2013.01); *G06T 2207/30041* (2013.01); *G06T 2207/30201* (2013.01)

(58) Field of Classification Search
    CPC ........... G06T 2207/30201; G06T 7/254; G06T 7/277; G06T 7/74
    See application file for complete search history.

(56) References Cited

FOREIGN PATENT DOCUMENTS

| | | | | |
|---|---|---|---|---|
| JP | 2007-271554 | | 10/2007 | |
| JP | 2008-029702 | | 2/2008 | |
| JP | 2008-246004 | | 10/2008 | |
| JP | 2008246004 | * | 10/2008 | ............. A61B 3/113 |
| JP | WO2012077713 | * | 6/2012 | ............. A61B 3/113 |
| WO | WO 2008/120321 A1 | | 10/2008 | |
| WO | WO 2012/020760 A1 | | 2/2012 | |
| WO | WO 2012/077713 A1 | | 6/2012 | |
| WO | WO 2014/073645 A1 | | 5/2014 | |

OTHER PUBLICATIONS

Extended European Search Report dated Jan. 4, 2018 issued in corresponding European Patent Application No. 15833722.0.

\* cited by examiner

Fig.12
(a)
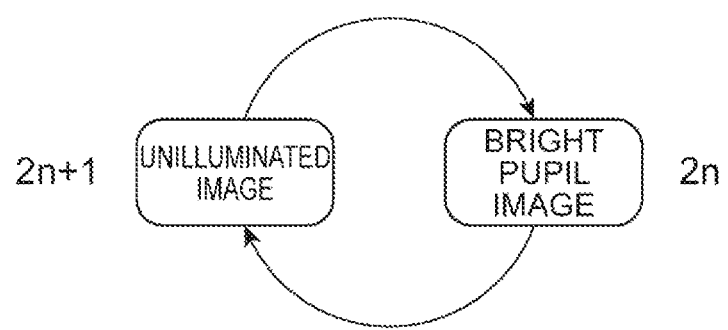
(b)
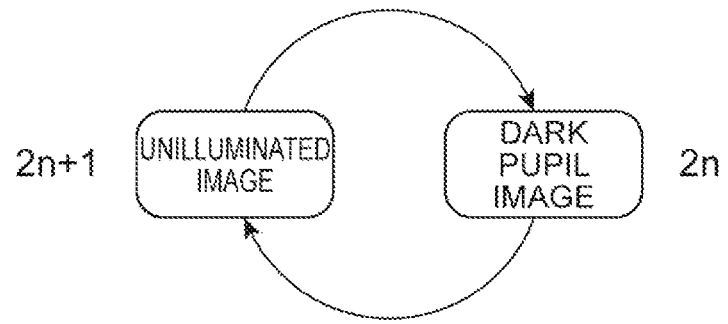

US 10,417,782 B2

CORNEAL REFLECTION POSITION ESTIMATION SYSTEM, CORNEAL REFLECTION POSITION ESTIMATION METHOD, CORNEAL REFLECTION POSITION ESTIMATION PROGRAM, PUPIL DETECTION SYSTEM, PUPIL DETECTION METHOD, PUPIL DETECTION PROGRAM, GAZE DETECTION SYSTEM, GAZE DETECTION METHOD, GAZE DETECTION PROGRAM, FACE ORIENTATION DETECTION SYSTEM, FACE ORIENTATION DETECTION METHOD, AND FACE ORIENTATION DETECTION PROGRAM

CROSS-REFERENCE TO RELATED APPLICATIONS

The present application is a 35 U.S.C. §§ 371 national phase conversion of PCT/JP2015/071270, filed Jul. 27, 2015, which claims priority to Japanese Patent Application No. 2014-169508, filed Aug. 22, 2014, the contents of which are incorporated herein by reference. The PCT International Application was published in the Japanese language.

TECHNICAL FIELD

The present invention relates to a corneal reflection position estimation system, a corneal reflection position estimation method, a corneal reflection position estimation program, a pupil detection system, a pupil detection method, a pupil detection program, a gaze detection system, a gaze detection method, a gaze detection program, a face orientation detection system, a face orientation detection method, and a face orientation detection program.

BACKGROUND ART

In the past, technique for detecting the pupil of a subject has been known. This technique is applicable to detection of a see-through driving, detection of drowsiness of a driver, investigation of the degree of interest of a product, data input to a computer, and the like.

With respect to such pupil detection technique, the following Patent Document 1 discloses a pupil detection method of detecting a pupil by acquiring a bright pupil image, an unilluminated image, and a dark pupil image and then performing image difference processing thereon. In this method, a corneal reflection image is detected from a difference image acquired by subtracting the unilluminated image from the bright pupil image or a difference image acquired by subtracting the unilluminated image from the dark pupil image. In these difference images, since only images by respective light sources are acquired, the corneal reflection can be easily detected by removing an image of ambient light (disturbance light) such as the sun. Therefore, the pupil can be detected by performing position correction based on corneal reflection with respect to the two difference images and subtracting the difference images from each other.

CITATION LIST

Patent Literature

[Patent Document 1] JP 2008-246004 A

SUMMARY OF INVENTION

Technical Problem

However, generally, a head of a subject moves while eyes of the subject are photographed one by one. In that case, since a false image due to disturbance light also moves, a false image (false corneal reflection) indistinguishable from true corneal reflection cannot be removed just by simply subtracting an unilluminated image from a bright pupil image (or a dark pupil image), and position correction based on corneal reflection cannot be performed. In order to solve such situations, it is necessary to perform position correction based on corneal reflection even when subtracting an unilluminated image from a bright pupil image (or a dark pupil image). However, since there is no true corneal reflection in the unilluminated image, the position correction cannot be performed.

Therefore, in order to perform position correction of a bright pupil image (or a dark pupil image) and an unilluminated image, it is preferable to estimate a corneal reflection position in the unilluminated image.

Solution to Problem

A corneal reflection position estimation system according to one aspect of the present invention includes: an image acquisition unit configured to continuously acquire an image of an eye of a subject by controlling a camera equipped with a light source, the image acquisition unit being configured to acquire a plurality of pupil images taken by using light from the light source and then acquire one unilluminated image taken without using light from the light source; and an estimation unit configured to calculate positions of corneal reflection or corneal sphere centers, which correspond to the plurality of pupil images, as reference positions, calculate a movement vector of the corneal reflection or the corneal sphere center based on the plurality of reference positions, and estimate the corneal reflection position in the unilluminated image based on at least the movement vector.

A corneal reflection position estimation method according to one aspect of the present invention is a corneal reflection position estimation method, which is performed by a corneal reflection position estimation system including a processor, the corneal reflection position estimation method including: an image acquisition step of continuously acquiring an image of an eye of a subject by controlling a camera equipped with a light source, the image acquisition step including acquiring a plurality of pupil images taken by using light from the light source and then acquiring one unilluminated image taken without using light from the light source; and an estimation step of calculating positions of corneal reflection or corneal sphere centers, which correspond to the plurality of pupil images, as reference positions, calculating a movement vector of the corneal reflection or the corneal sphere center based on the plurality of reference positions, and estimating the corneal reflection position in the unilluminated image based on the movement vector.

A corneal reflection position estimation program according to one aspect of the present invention causes a computer to function as: an image acquisition unit configured to continuously acquire an image of an eye of a subject by controlling a camera equipped with a light source, the image acquisition unit being configured to acquire a plurality of pupil images taken by using light from the light source and then acquire one unilluminated image taken without using light from the light source; and an estimation unit configured to calculate positions of corneal reflection or corneal sphere centers, which correspond to the plurality of pupil images, as reference positions, calculate a movement vector of the corneal reflection or the corneal sphere center based on the plurality of reference positions, and estimate the corneal reflection position in the unilluminated image based on at least the movement vector.

In this aspect, the plurality of reference positions (positions of corneal reflection or corneal sphere centers) corresponding to the plurality of pupil images acquired before the unilluminated image is calculated. Since the pupil image is taken by using light from the light source, the position of the corneal reflection or the corneal sphere center can be obtained from the pupil image. Then, since the movement of the corneal reflection or the corneal sphere center immediately before the acquisition of the unilluminated image can be grasped by obtaining the movement vector of the corneal reflection or the corneal sphere center from the plurality of reference positions, the corneal reflection position of the time point when the unilluminated image was acquired can be estimated from the movement.

Advantageous Effects of Invention

According to one aspect of the present invention, it is possible to estimate a corneal reflection position in an unilluminated image.

Figure 1:
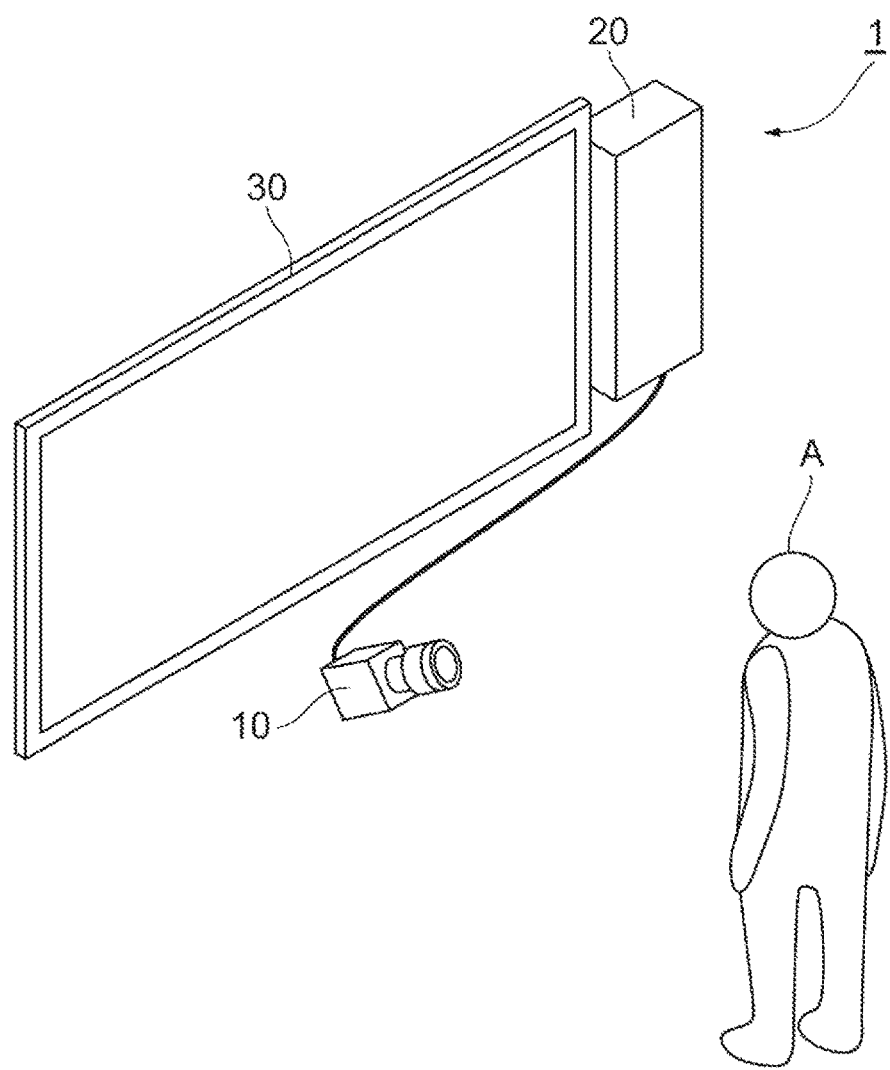
FIG. 1 is a perspective view illustrating a detection system according to a first embodiment.

The (a) and (b) of FIG. 12 are diagrams illustrating acquisition of an image according to a modification.

DESCRIPTION OF EMBODIMENTS

Hereinafter, embodiments of the present invention will be described in detail with reference to the accompanying drawings. In the following embodiments, a corneal reflection position estimation system and a pupil detection system according to the present invention are applied to a detection system 1. Note that, in the description of the drawings, the same elements are denoted by the same reference numerals and a redundant description thereof will be omitted.

[First Embodiment]
<Configuration of Detection System>

A configuration of a detection system 1 according to an embodiment will be described with reference to FIGS. 1 to 4. The detection system 1 is a computer system that detects a pupil of a subject, and a corneal reflection position estimation method and a pupil detection method according the present embodiments are performed by the system. The subject is a person of which the pupil is to be detected, and can be referred to as a subject person. The use purpose of the detection system 1, the corneal reflection position estimation method, and the pupil detection method is not limited at all, and the detection system 1 can be used for, for example, detection of inattentive driving, detection of driver's drowsiness, investigation of degree of interest in products, data input to computer, etc.

The detection system 1 includes one camera 10 and an image processing device 20. In the present embodiment, the detection system 1 further includes a display device 30 which is a subject viewed by a subject A. However, since the use purpose of the detection system 1 is not limited, objects in a gaze direction of the subject A are not limited to the display device 30 and may be, for example, a front glass of a vehicle. Therefore, the display device 30 is not an essential element in the detection system 1. The camera 10 is connected to the image processing device 20 in a wireless or wired manner and various types of data or commands are transmitted between the camera 10 and the image processing device 20. Camera calibration is performed in advance with respect to the camera 10.

The camera 10 is used to photograph eyes of the subject A and its surroundings. The camera 10 is disposed at a position lower than the face of the subject A in order to prevent reflected light from being taken in a face image when the subject A is wears glasses. An elevation angle of the camera 10 in a horizontal direction is set to be in a range from 20 degrees to 35 degrees in consideration of both reliable detection of eyes and avoidance of interference of the visual field of the subject A.

In the present embodiment, a frame rate of each camera 10 is 240 fps (frames per second). In this case, the camera 10 can acquire an image every about 4.2 ms. The camera 10 images the subject A in response to a command from the image processing device 20 and outputs image data to the image processing device 20.

Figure 2:
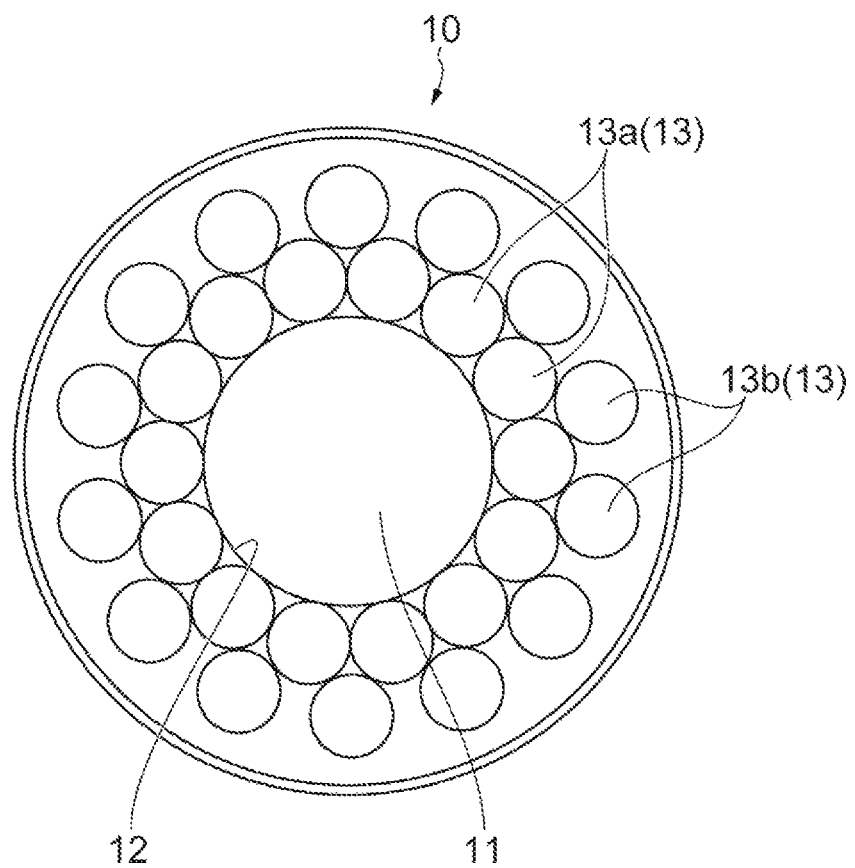
FIG. 2 is a plan view illustrating a lens portion of a camera.

The lens portion of the camera 10 is schematically illustrated in FIG. 2. As illustrated in FIG. 2, in the camera 10, an objective lens 11 is accommodated in an aperture 12 having a circular shape, and a light source 13 is provided on the outside of the aperture 12. The light source 13 is a device which irradiates with illumination light toward a face of the subject A and includes a plurality of light-emitting elements 13a and a plurality of light-emitting elements 13b. The light-emitting elements 13a are semiconductor light-emitting elements (LED) in which output light has a central wavelength of 850 nm and are arranged in a ring shape at equal intervals along the edges of the aperture 12. The light-emitting elements 13b are semiconductor light-emitting elements in which output light has a central wavelength of 940 nm and are arranged in a ring shape at equal intervals on the outside of the light-emitting elements 13a. Therefore, a distance from an optical axis of the camera 10 to the light-emitting elements 13b is larger than a distance from the optical axis to the light-emitting elements 13a. Each of the light-emitting elements 13a and 13b are provided to emit illumination light along the optical axis of the camera 10. Also, the arrangement of the light source 13 is not limited to the configuration illustrated in FIG. 2 and another arrangement is possible as long as the camera can be regarded as a pinhole model.

The image processing device 20 is a computer that performs control of the camera 10 and detection of a pupil of the subject A. The image processing device 20 may be implemented by a stationary or portable personal computer (PC), a workstation, or another type of computer. Also, the image processing device 20 may be implemented by combining a plurality of computers of arbitrary types. In the case of using a plurality of computers, the computers are connected via a communication network, such as Internet or intranet.

Figure 3:
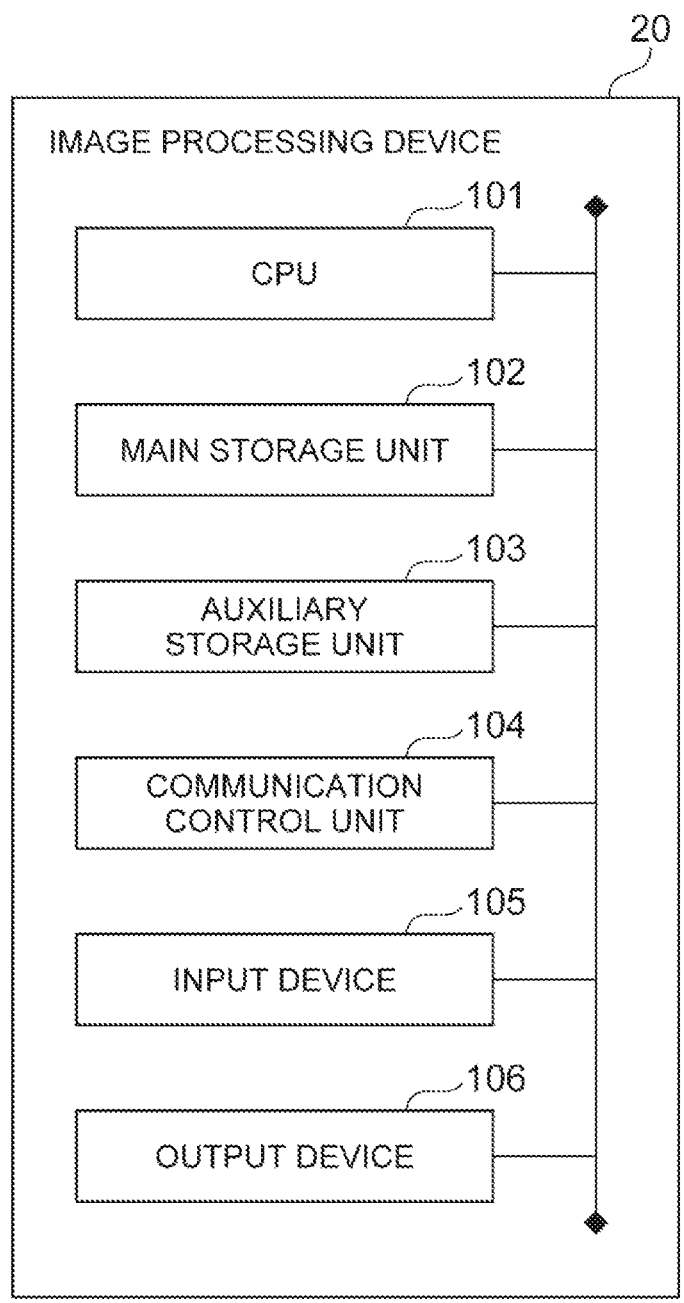
FIG. 3 is a diagram illustrating a hardware configuration of an image processing device illustrated in FIG. 1.

A general hardware configuration of the image processing device 20 is illustrated in FIG. 3. The image processing device 20 includes a CPU (processor) 101 which performs an operating system or an application, a program or the like, a main storage unit 102 which is configured by ROM and RAM, an auxiliary storage unit 103 which is configured by a hard disk, a flash memory or the like, a communication control unit 104 which is configured by a network card or a wireless communication module, an input device 105, such as a keyboard or a mouse, or the like, and an output device 106, such as a display, a printer, or the like.

Each functional element of the image processing device 20 to be described below is implemented by loading predetermined software on the CPU 101 or the main storage unit 102, operating the communication control unit 104 or the input device 105, the output device 106, or the like, under the control of the CPU 101, and reading and writing data in the main storage unit 102 or the auxiliary storage unit 103. Data or database necessary for processing is stored in the main storage unit 102 and the auxiliary storage unit 103.

Figure 4:
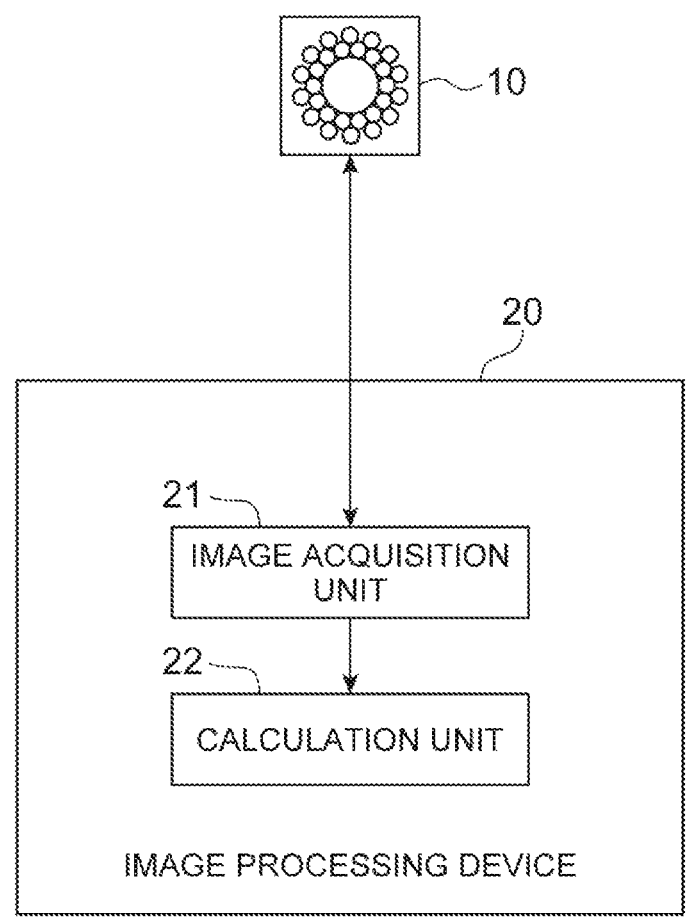
FIG. 4 is a block diagram illustrating a functional configuration of the detection system illustrated in FIG. 1.

As illustrated in FIG. 4, the image processing device 20 includes an image acquisition unit 21 and a calculation unit 22 as functional elements. The image acquisition unit 21 is a functional element that acquires image data, in which at least the eye of the subject A is imaged, from the camera 10 by controlling an image pickup timing of the camera 10 and a light emission timing of the light source 13 of the camera 10. The calculation unit 22 is a functional element that calculates a pupil position of the subject A based on the image data.

The output destination of processing results by the image processing device 20 is not limited at all. For example, the image processing device 20 may display the processing results on a monitor in an image, figure, or text form, may store the processing results in a storage unit, such as memory or database, or may transmit the processing results to another computer system via a communication network. Alternatively, the image processing device 20 may further perform arbitrary processing based on the results.

<Estimation of Corneal Reflection and Detection of Pupil>

Next, with reference to FIGS. 5 to 8, the operation of the detection system 1 will be described and the corneal reflection position estimation method and the pupil detection method according to the present embodiments will be described.

(Acquisition of Pupil Image)

Light entering an eye is irregularly reflected by a retina and light passing through a pupil from among the reflected light has strong directivity, and therefore, represents characteristics of returning to a light source. When the camera is exposed to the light in a case in which the light source disposed in the vicinity of the aperture of the camera emits light, a part of light reflected from the retina enters the aperture, thus obtaining an image in which the pupil is imaged more brightly than the vicinity of the pupil. The image is the bright pupil image. On the other hand, when the camera is exposed to the light in a case in which the light source spaced apart from the aperture of the camera emits light, light entering an eye does not almost return to the aperture of the camera, thus obtaining an image in which the pupil is darkly imaged. The image is the dark pupil image. Also, when an eye is irradiated with light having a wavelength of high transmittance, the pupil is brightly photographed because the large amount of light is reflected by a cornea, and when an eye is irradiated with light having a wavelength of low transmittance, the pupil is darkly photographed because the small amount of light is reflected by a cornea. An image acquired by exposing the camera without turning on any light source of the camera is an unilluminated image, and the unilluminated image also is a type of the pupil image.

In the present embodiment, the light-emitting element 13a emitting light having a wavelength of high transmittance (central wavelength is 850 nm) is disposed at a position adjacent to the aperture 12, and the light-emitting element 13b emitting light having a wavelength of low transmittance (central wavelength is 940 nm) is disposed at a position spaced apart from the aperture 12. The image acquisition unit 21 takes a bright pupil image by turning on the light-emitting element 13a, takes a dark pupil image by turning on the light-emitting element 13b, and takes an unilluminated image without turning on the light-emitting elements 13a and 13b. Therefore, the bright pupil image and the dark pupil image are pupil images acquired by image pickup using light from the light source 13, and the unilluminated image is a pupil image acquired by image pickup without using light from the light source 13.

The image acquisition unit 21 acquires the bright pupil image, the dark pupil image, and the unilluminated image by controlling the camera 10 and outputs these images to the calculation unit 22. In the present embodiment, the image acquisition unit 21 repeats a process of acquiring the pupil image in the order of "bright pupil image->unilluminated image->dark pupil image->unilluminated image".

(Detection of Pupil Position)

The calculation unit 22 obtains a pupil center of one eye or both eyes of the subject A based on the pupil image input from the image acquisition unit 21.

When an i-th acquired bright pupil image (or dark pupil image) and an (i+1)-th acquired dark pupil image (or bright pupil image) are acquired, if the head of the subject A does not move while the two pupil images are acquired, a difference image in which a pupil portion emerges can be generated just by taking a difference between the bright pupil image and the dark pupil image. However, if the head of the subject A moves in a short time until the two pupil images are taken, misalignment occurs at the position of the pupil between the two images. Consequently, an excellent difference image cannot be acquired. Therefore, before the difference image is acquired, the calculation unit 22 performs position correction based on corneal reflection (hereinafter, simply referred to as "position correction") with respect to the bright pupil image and the dark pupil image.

Figure 5:
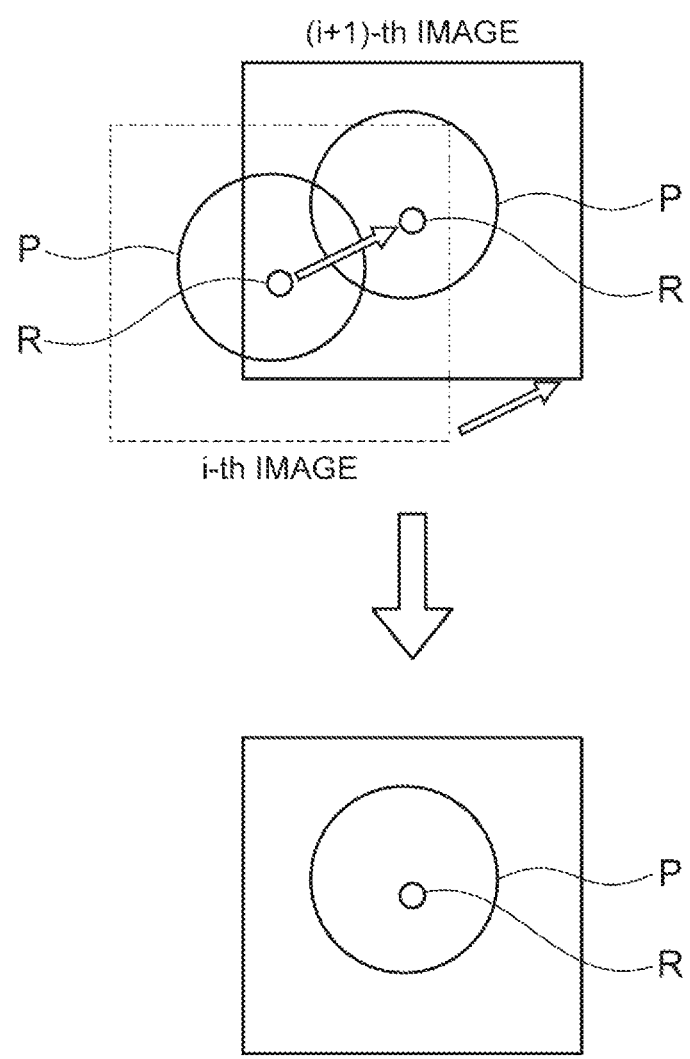
FIG. 5 is a diagram for describing position correction based on corneal reflection.

As illustrated in FIG. 5, the calculation unit 22 takes a difference between the two images after shifting the i-th image (refer to arrows in FIG. 5) such that the positions of corneal reflection points R respectively detected from the i-th image and the (i+1)-th image matched each other. It is possible to detect a pupil P from the difference image illustrated in the lower end of FIG. 5. More specifically, the calculation unit 22 generates the difference image by performing position correction on a region including the pupil and the corneal reflection. This region is referred to as a window. A window setting method is not limited. As one example, a position of corneal reflection may be set as a center and a small region including the pupil may be set as the window. The position correction is a process of shifting one of images in two windows so as to match the position of the corneal reflection. Subsequently, by using the fact that there is no great change in brightness from a previous image, the calculation unit 22 performs binarization of the difference image by setting a half value of mean brightness as a threshold value by using the brightness mean of the pupil detected from the previous image, and perform labeling thereon. Subsequently, the calculation unit 22 selects pupil candidates from among connection components of labeled pixels based on shape parameters, such as a pupil-like area, size, area ratio, square degree, and pupil feature amount. Then, the calculation unit 22 determines a pupil candidate having the largest area among the pupil candidates as the pupil and obtains central coordinates of the pupil. The calculation unit 22 can also obtain an accurate corneal reflection position based on the central coordinates of the pupil.

However, the method of detecting the pupil from the difference image directly obtained from the bright pupil image and the dark pupil image is easily affected by disturbance light, and false corneal reflection appears on the difference image due to the disturbance light. In many cases, it is difficult to distinguish true corneal reflection from false corneal reflection by features of the image alone.

In order to solve this problem, the detection system 1 acquires the unilluminated image in addition to the bright pupil image and the dark pupil image and generates a difference bright pupil image and a difference dark pupil image. In principle, it is possible to obtain the bright pupil image and the dark pupil image in which only the true conical reflection by illumination of the light source of the camera 10 is photographed (that is, the difference bright pupil image and the difference dark pupil image) by performing the difference using the unilluminated image to remove the false corneal reflection caused by external light such as sunlight. Therefore, an excellent difference image for detecting the pupil can be acquired by performing position correction on the difference bright pupil image and the difference dark pupil image.

Figure 6:
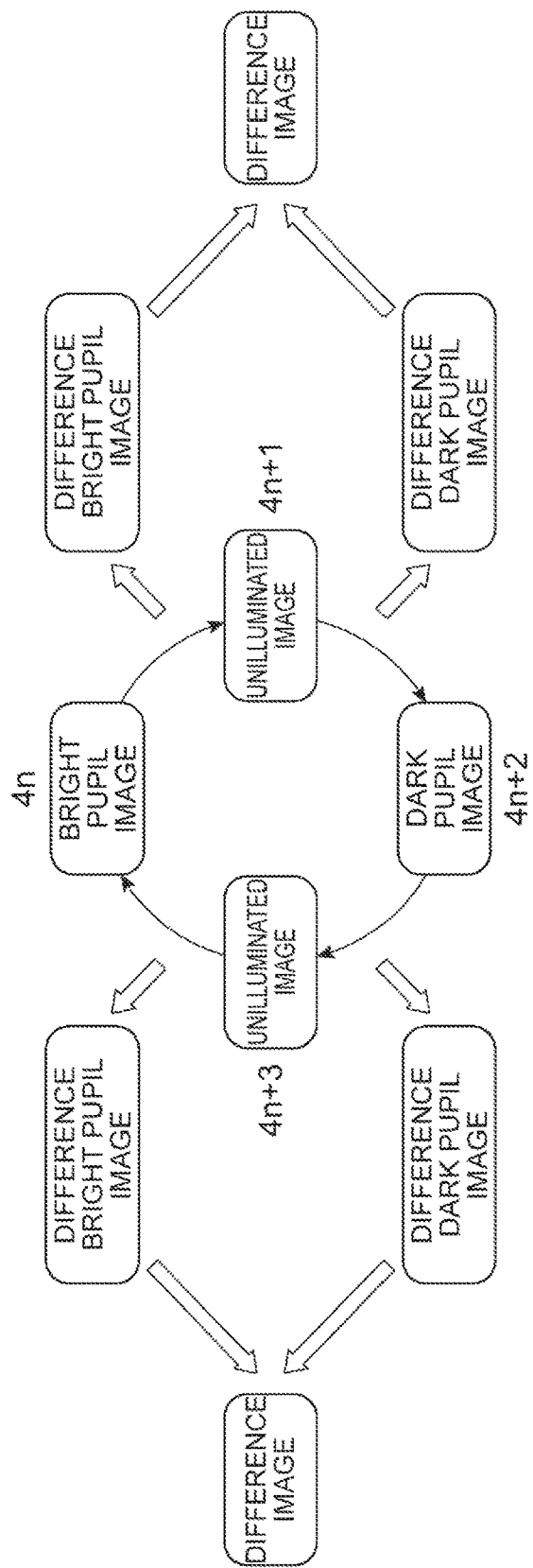
FIG. 6 is a diagram illustrating acquisition and generation of an image according to a first embodiment.

In the present embodiment in which the unilluminated image is necessarily acquired between the bright pupil image and the dark pupil image, the difference image is acquired by the procedure of FIG. 6. That is, the calculation unit 22 acquires the difference bright pupil image by taking the difference between the continuously acquired bright pupil image and unilluminated image and acquires the difference dark pupil image by taking the difference between the continuously acquired dark pupil image and unilluminated image. Subsequently, the calculation unit 22 acquires the difference image by taking the difference between the continuously acquired difference bright pupil image and difference dark pupil image. Then, the calculation unit 22 obtains the central coordinates of the pupil (detects the pupil) based on the difference image. The calculation unit 22 may use subtraction or division when acquiring the difference image from the difference bright pupil image and the difference dark pupil image. The "difference image" in the present specification is a concept including not only an image acquired by subtraction but also a division image acquired by division.

However, in a case where the frame rate of the camera 10 is about 240 fps as in the present embodiment, a time difference from the acquisition of the i-th image to the acquisition of the (i+1)-th image is about 4.2 ms. If this time difference occurs, there occurs a case that cannot ignore the movement of the head of the subject A during the acquisition of the bright pupil image and the unilluminated image for acquiring the difference bright pupil image. For example, in a case where an automobile runs on a rough road, if a head vibrates fast, the positions of pupil and corneal reflection may be greatly changed between two successive images. When the difference bright pupil image is generated without considering the movement of the head, the false corneal reflection cannot be removed in that image. This phenomenon may also occur in the difference dark pupil image.

Figure 7:
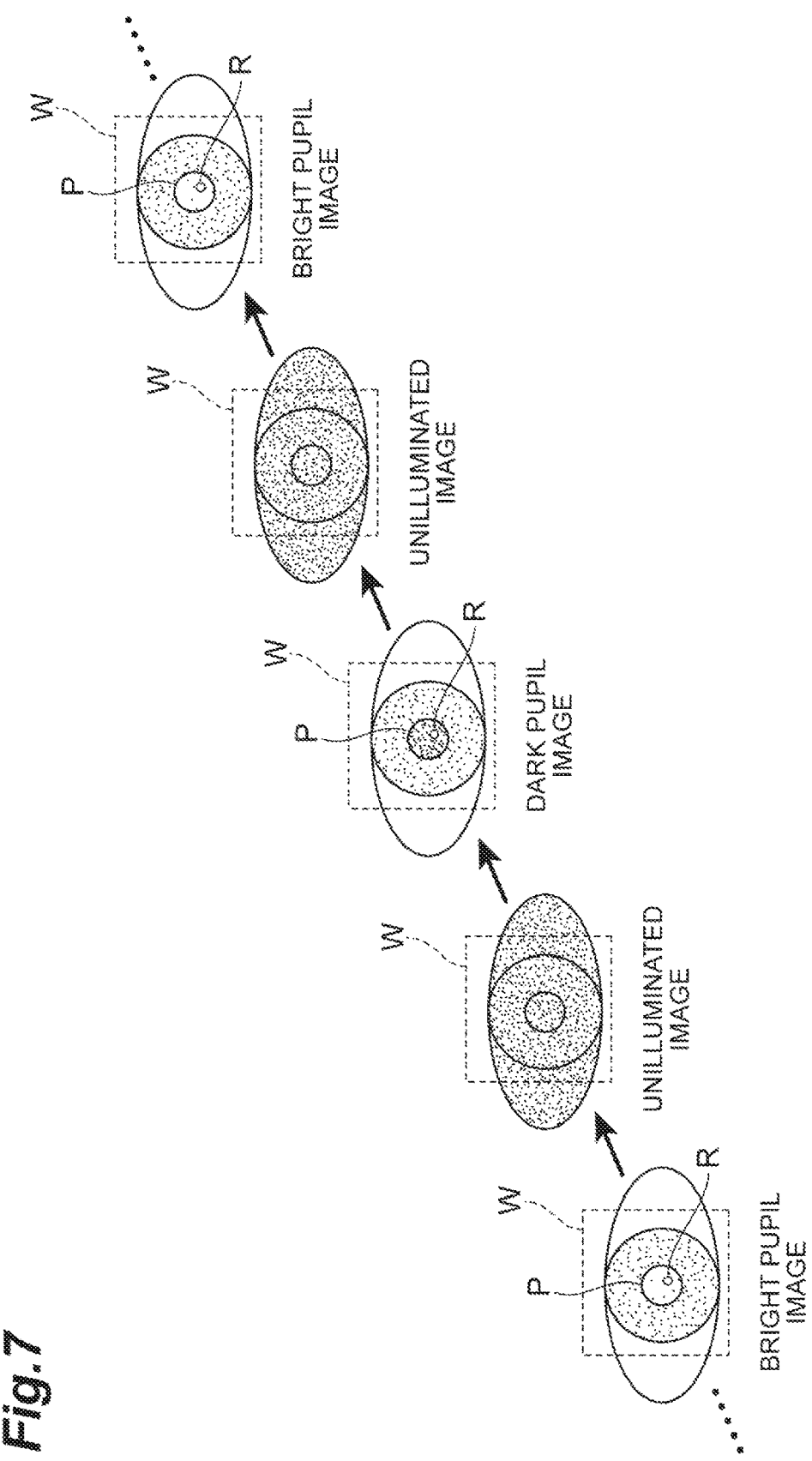
FIG. 7 is a diagram illustrating movement of a pupil.

In order to solve such a problem, it is necessary to perform position correction on the bright pupil image (or the dark pupil image) and the unilluminated image when generating the difference bright pupil image (or the difference dark pupil image). However, as illustrated in FIG. 7, since the true conical reflection R is not present in the unilluminated image, it is impossible to perform position correction on a set of the unilluminated image and the adjacent bright pupil image or dark pupil image. Therefore, the calculation unit 22 estimates the position of true corneal reflection in the unilluminated image. Then, the calculation unit 22 performs position correction on two adjacent windows w (that is, shifts the image in the previous window so that the corneal reflection in the previous window w matches the conical reflection in the later window w), and acquires the difference bright pupil image or the difference dark pupil image from the two windows w.

(Estimation of Conical Reflection Position in Case where Image Acquisition Interval is Constant)

As illustrated in FIG. 6, a process of acquiring four images (bright pupil image->unilluminated image->dark pupil image->unilluminated image) is set as 1-cycle process. When the cycle number is represented by an integer equal to or greater than 0, in an n-th cycle, a 4n-th image is a bright pupil image, a (4n+1)-th image is an unilluminated image, a (4n+2)-th image is a dark pupil image, and a (4n+3)-th image is an unilluminated image.

In a case where the pupil image acquisition interval by the image acquisition unit 21 is constant, the calculation unit 22 estimates the conical reflection position by the following method.

The calculation unit 22 obtains a corneal reflection position $X_{4n}$ in the bright pupil image by detecting the conical reflection from the difference bright pupil image acquired from the 4n-th image (bright pupil image) and the (4n+1)-th image (unilluminated image). Furthermore, the calculation unit 22 obtains a corneal reflection position $X_{4n+2}$ in the dark pupil image by detecting the corneal reflection from the difference dark pupil image acquired from the (4n+2)-th image (dark pupil image) and the (4n+1)-th image (unilluminated image). It is assumed that the corneal reflection positions $X_{4n}$ and $X_{4n+2}$ have been finally determined in the previous process. In the present embodiment, the corneal reflection position is represented by two-dimensional coordinates (x, y) on the image.

On the assumption that the two corneal reflection positions have been determined, the calculation unit 22 estimates the corneal reflection position $X_{4n+3}$ in the (4n+3)-th image (unilluminated image) by using a constant velocity model expressed by the following Formula (1). The corneal reflection position $X_{4n+3}$ corresponds to the position of true corneal reflection occurring when the light source of the camera 10 is turned on.

$$X_{4n+3} = X_{4n+2} + \tfrac{1}{2}(X_{4n+2} - X_{4n}) \quad (1)$$

Formula (1) means that the conical reflection position in the processing target image when assuming that the movement (movement vector $(X_{4n+2} - X_{4n})$) of the corneal reflection position between the bright pupil image and the dark pupil image acquired immediately before the (4n+3)-th image (unilluminated image) is continued up to the (4n+3)-th image as it is. The "movement vector" in the present embodiment is a vector indicating the direction and amount of the movement of the corneal reflection position. Also, in the present embodiment, a reference position used for calculating the movement vector is the corneal reflection position.

Figure 8:
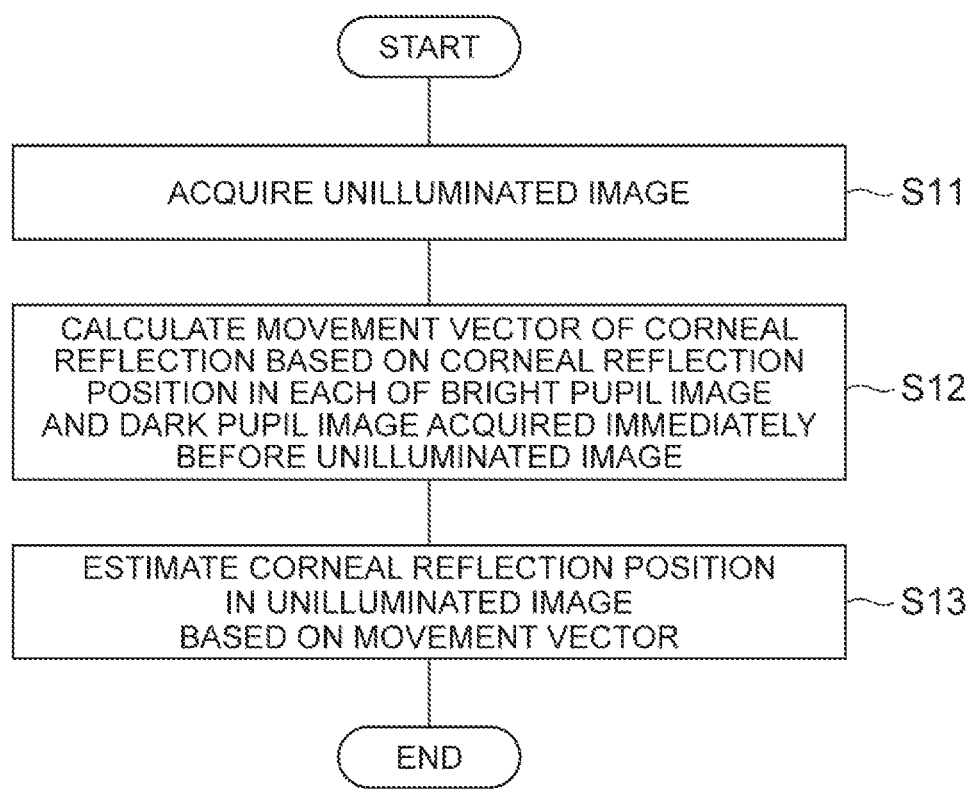
FIG. 8 is a flowchart of a method of estimating corneal reflection in an unilluminated image.

The procedure of estimating the corneal reflection position in the unilluminated image can be represented by the flowchart of FIG. 8. That is, when the image acquisition unit 21 acquires the unilluminated image (step S11, image acquisition step), the calculation unit 22 calculates the movement vector of the corneal reflection based on the corneal reflection positions in the bright pupil image and the dark pupil image acquired immediately before the unilluminated image (step S12, estimation step). Then, the calculation unit 22 estimates the corneal reflection position in the unilluminated image based on the movement vector (step S13, estimation step). As such, the calculation unit 22 functions as an estimation unit which estimates the corneal reflection position in the unilluminated image.

Similarly, the calculation unit 22 estimates the corneal reflection position $X_{4(n+1)}$ in the {4(n+1)}-th image, which is the next bright pupil image, by using a constant velocity model expressed by the following Formula (2).

$$X_{4(n+1)} = X_{4n+2} + (X_{4n+2} - X_{4n}) \quad (2)$$

Formula (2) means that the corneal reflection position in the processing target image when assuming that the movement (movement vector $(X_{4n+2} - X_{4n})$) of the corneal reflection is continued up to the {(4(n+1)}-th image as it is.

When the corneal reflection position $X_{4n+3}$ is estimated, the calculation unit 22 generates the difference dark pupil image by performing position correction on the (4n+2)-th image (dark pupil image) and the (4n+3)-th image (unilluminated image) (that is, by shifting the dark pupil image toward the unilluminated image by $\Delta X_{4n+2} = X_{4n+3} - X_{4n+2}$), and detects the corneal reflection from the difference dark pupil image. Furthermore, when the corneal reflection position $X_{4(n+1)}$ is estimated, the calculation unit 22 generates the difference bright pupil image by performing position correction on the (4n+3)-th image (unilluminated image) and the {(4(n+1)}-th image (bright pupil image) (that is, by shifting the unilluminated image toward the bright pupil image by $\Delta X_{4n+3} = X_{4(n+1)} - X_{4n+3}$), and detects the corneal reflection from the difference bright pupil image. Then, the calculation unit 22 generates the difference image by performing position correction on the difference dark pupil image and the difference bright pupil image and obtains central coordinates of the pupil (detects the pupil) from the difference image. Furthermore, the calculation unit 22 also obtains an accurate corneal reflection position $X_{4(n+1)}$ based on the central coordinates of the pupil, and the corneal reflection position $X_{4(n+1)}$ is determined thereby.

As a result, the corneal reflection position $X_{4n+2}$ in the (4n+2)-th image (dark pupil image) and the corneal reflection position $X_{4(n+1)}$ in the {4(n+1)}-th image (bright pupil image) are obtained. Therefore, the calculation unit 22 can estimate the corneal reflection position $X_{4(n+1)+1}$ in the {4(n+1)+1}-th image (unilluminated image) and the corneal reflection position $X_{4(n+1)+2}$ in the {4(n+1)+2}-th image (dark pupil image) by using a constant velocity model expressed by the following Formulae (3) and (4).

$$X_{4(n+1)+1} = X_{4(n+1)} + \tfrac{1}{2}(X_{4(n+1)} - X_{4n+2}) \quad (3)$$

$$X_{4(n+1)+2} = X_{4(n+1)} + (X_{4(n+1)} - X_{4n+2}) \quad (4)$$

When the corneal reflection position $X_{4(n+1)+1}$ is estimated, the calculation unit 22 generates the difference bright pupil image by performing position correction on the {4(n+1)}-th image (bright pupil image) and the {(4(n+1)+1}-th image (unilluminated image) and detects the corneal reflection from the difference bright pupil image. After that, when the corneal reflection position $X_{4(n+1)+2}$ is estimated, the calculation unit 22 generates the difference dark pupil image by performing position correction on the {4(n+1)+1}-th image (unilluminated image) and the {(4(n+1)+2}-th image (dark pupil image) and detects the corneal reflection from the difference dark pupil image. Then, the calculation unit 22 generates the difference image by performing position correction on the difference bright pupil image and the difference dark pupil image and obtains central coordinates of the pupil from the difference image. Also, the calculation unit 22 also obtains an accurate corneal reflection position $X_{4(n+1)+2}$ based on the central coordinates of the pupil, and the corneal reflection position $X_{4(n+1)+2}$ is determined thereby.

The calculation unit 22 can track the position of the pupil by repeating the above processes.

(Estimation of Corneal Reflection Position in Case where Image Acquisition Interval is not Constant)

In the descriptions representing the above Formulae (1) to (4), it has been assumed that the image acquisition interval was constant. However, in practice, various image acquisition intervals may occur. For example, for reasons that it may take a lot of time for image processing or a timing of image processing is delayed because a multitask OS of the image processing device 20 performs another processing, it may be impossible to acquire an image at a predetermined timing (for example, at intervals of about 4.2 ms) (missing image), or there may occur a situation in which a desired image is barely acquired by several retrials. In this case, the image acquisition interval may be changed (for example, the interval may be about 8.4 (=4.2×2) ms or about 12.6 (=4.2×3) ms). On the other hand, in a case where the image processing device 20 adopts external synchronization to transmit a next image acquisition command to the camera 10 at the stage of finishing a processing for a certain image, missing image does not occur. However, in this case, the image acquisition interval may be irregular depending on the status of hardware in the image processing device 20 (for example, an operating status of a CPU).

In consideration of such cases, the calculation unit 22 may measure the acquisition times of individual images and estimate the corneal reflection position by using the constant velocity model considering the image acquisition interval obtained from that acquisition times.

It is assumed that the time interval from the acquisition of the 4n-th image (bright pupil image) to the acquisition of the (4n+1)-th image (unilluminated image) is $\Delta t_1''$, and the time interval from the acquisition of the unilluminated image to the acquisition of the (4n+2)-th image (dark pupil image) is $\Delta t_2''$. Also, it is assumed that the time interval from the acquisition of the dark pupil image to the acquisition of the (4n+3)-th image (unilluminated image) is $\Delta t_3''$, and the time interval from the acquisition of the unilluminated image to the acquisition of the {4(n+1)}-th image (bright pupil image) is $\Delta t_4''$. The time interval may be a difference between an exposure start time when a certain image is acquired and an exposure start time when a next image is acquired, may be a difference between exposure end times, or may be a difference between image transmission start times or image transmission end times from the camera 10 to the image processing device 20.

In this case, the calculation unit 22 estimates the corneal reflection positions $X_{4n+3}$, $X_{4(n+1)}$, $X_{4(n+1)+1}$, and $X_{4(n+1)+2}$ by using a constant velocity model expressed by the following Formulae (5) to (8). These Formulae (5) to (8) correspond to Formulae (1) to (4). Therefore, even when the image acquisition interval is various, the calculation unit 22 can generate the difference bright pupil image and the difference dark pupil image, from which false corneal reflection is removed, and can detect the pupil by generating the difference image from the two images.

[Math. 1]
$$X_{4n+3} = X_{4n+2} + \frac{\Delta t_3^n}{\Delta t_1^n + \Delta t_2^n}(X_{4n+2} - X_{4n}) \quad (5)$$

[Math. 2]
$$X_{4(n+1)} = X_{4n+2} + \frac{\Delta t_3^n + \Delta t_4^n}{\Delta t_1^n + \Delta t_2^n}(X_{4n+2} - X_{4n}) \quad (6)$$

[Math. 3]
$$X_{4(n+1)+1} = X_{4(n+1)} + \frac{\Delta t_1^{n+1}}{\Delta t_3^n + \Delta t_4^n}(X_{4(n+1)} - X_{4n+2}) \quad (7)$$

[Math. 4]
$$X_{4(n+1)+2} = X_{4(n+1)} + \frac{\Delta t_1^{n+1} + \Delta t_2^{n+1}}{\Delta t_3^n + \Delta t_4^n}(X_{4(n+1)} - X_{4n+2}) \quad (8)$$

In a case where the image is assumed to be missed, the time intervals $\Delta t_1''$, $\Delta t_2''$, $\Delta t_3''$, and $\Delta t_4''$ may be represented by the number of frames necessary from the acquisition of a certain image to the acquisition of a next image. For example, if a frame number of the 4n-th image (bright pupil image) is 10 and a frame number of the (4n+1)-th image (unilluminated image) is 13, the time interval $\Delta t_1''$ is represented by 3 (=13−10). The time interval may be represented by a value obtained by multiplying the time interval of two adjacent frames (if the frame rate of the camera 10 is 240 fps, the time interval is about 4.2 ms) by the number of frames. However, in the calculation of Formulae (5) to (8), since the time interval between the two frames disappears due to reduction of fraction, the time intervals $\Delta t_1''$, $\Delta t_2''$, $\Delta t_3''$, and $\Delta t_4''$ can be represented by the number of frames.

If the image acquisition time in Formulae (5) to (8) is constant, these Formulae result in Formulae (1) to (4). Therefore, like Formulae (5) to (8), Formulae (1) to (4) mean the estimation of the corneal reflection position in the unilluminated image or the pupil image based on the movement vector and each individual time interval when each image is acquired.

<Detection Program>

Figure 9:
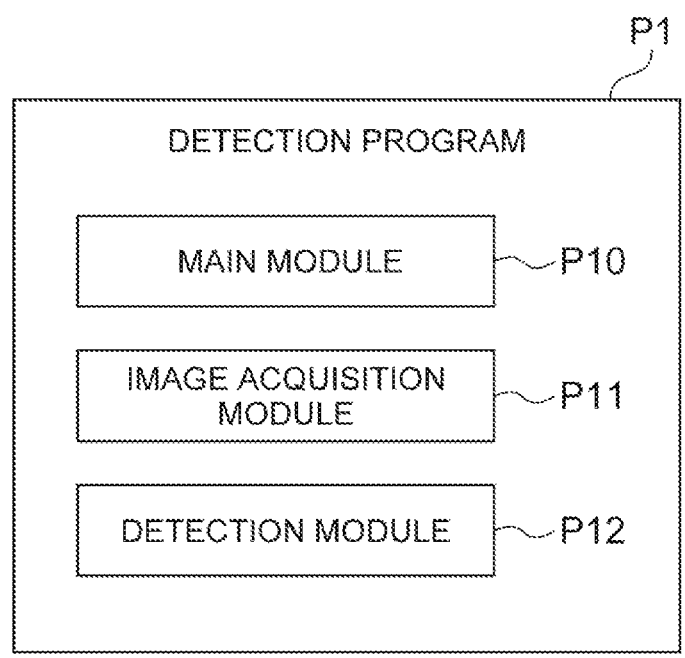
FIG. 9 is a diagram illustrating a configuration of a detection program according to a first embodiment.

Next, a detection program (corneal reflection position estimation program and pupil detection program) P1 for realizing the image processing device 20 will be described with reference to FIG. 9.

The detection program P1 includes a main module P10, an image acquisition module P11, and a calculation module P12.

The main module P10 is a part for comprehensively controlling a pupil detection function including a corneal reflection position estimation function. Functions realized by performing the image acquisition module P11 and the calculation module P12 are identical to those of the image acquisition unit 21 and the calculation unit 22.

The detection program P1 may be provided in the form of being fixedly recorded on a tangible recording medium such as, for example, CD-ROM, DVD-ROM, semiconductor memory, and the like. The detection program P1 may also be provided through a communication network as data signals superimposed on a carrier.

[Second Embodiment]

Figure 10:
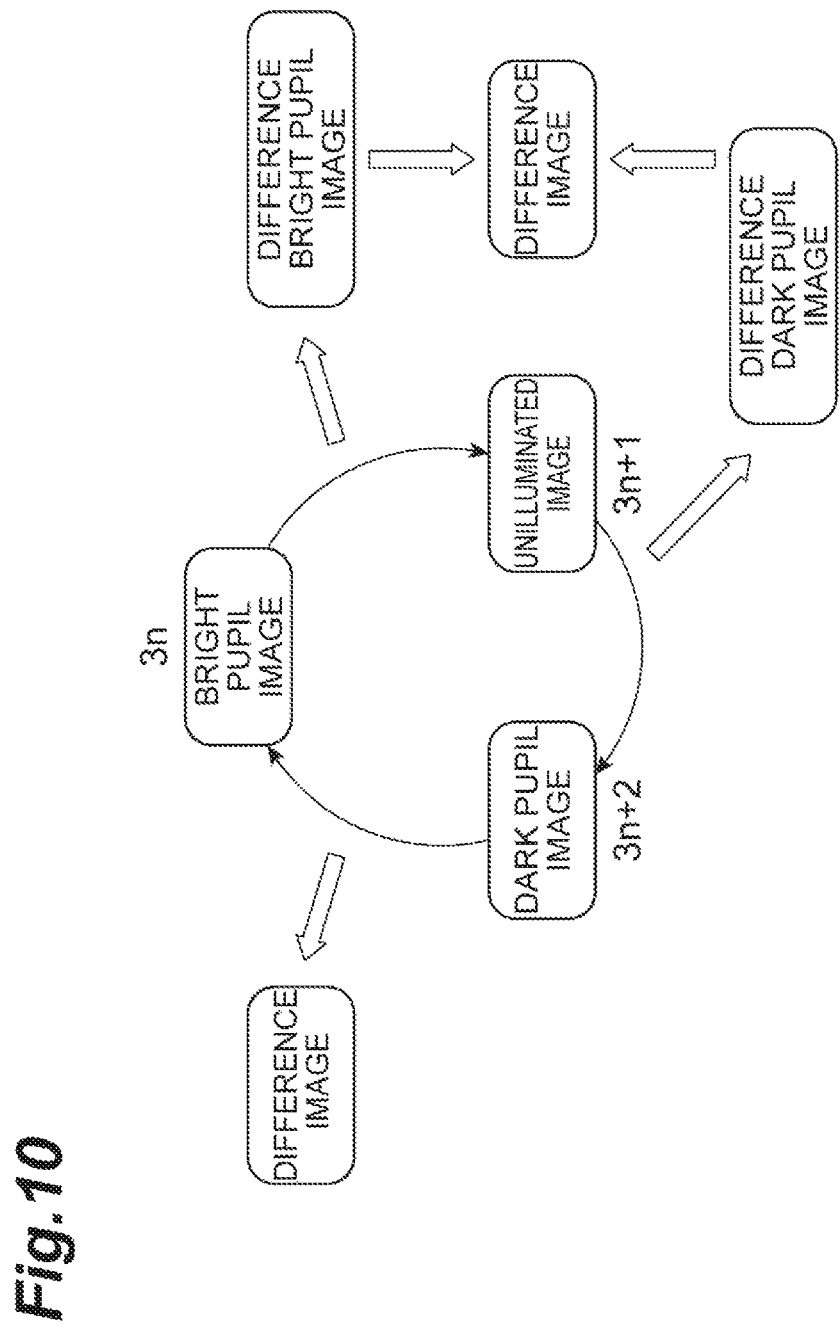
FIG. 10 is a diagram illustrating acquisition and generation of an image according to a second embodiment.

In the first embodiment, the image processing device 20 acquires four images (bright pupil image->unilluminated image->dark pupil image->unilluminated image) in one cycle, but the image acquisition method is not limited thereto. In the present embodiment, as illustrated in FIG. 10, the image processing device 20 may acquire an unilluminated image between a bright pupil image and a dark pupil image so as to acquire a bright pupil image (or a dark pupil image) every three sheets. In this case, the calculation unit 22 acquires a difference bright pupil image by taking a difference between a 3n-th acquired bright pupil image and a (3n+1)-th acquired unilluminated image and acquires a difference dark pupil image by taking a difference between the unilluminated image and a (3n+2)-th acquired dark pupil image. Then, the calculation unit 22 acquires a difference image by taking a difference between the difference bright pupil image and the difference dark pupil image. The calculation unit 22 may acquire an additional difference image by taking a difference between the continuously acquired dark pupil image and bright pupil image (for example, a (3n+2)-th acquired dark pupil image and a 3(n+1)-th acquired bright pupil image).

As such, in a case where the three images are acquired in one cycle, the calculation unit 22 estimates a corneal reflection position in an unilluminated image as follows.

The calculation unit 22 obtains a corneal reflection position $X_{3n}$ in the bright pupil image by detecting the corneal reflection from the difference bright pupil image acquired from the 3n-th acquired bright pupil image and the (3n+1)-th acquired unilluminated image. Furthermore, the calculation unit 22 obtains a corneal reflection position $X_{3n+2}$ in the dark pupil image by detecting the corneal reflection from the difference dark pupil image acquired from the (3n+2)-th acquired dark pupil image and the (3n+1)-th acquired unilluminated image. It is assumed that the corneal reflection positions $X_{3n}$ and $X_{3n+2}$ have been finally determined in the previous process. Here, the corneal reflection position is represented by two-dimensional coordinates (x, y) on the image. Based on the two corneal reflection positions, the calculation unit 22 estimates a corneal reflection position $X_{3(n+1)}$ in the {3(n+1)}-th acquired bright pupil image and a corneal reflection position $X_{3(n+1)+1}$ in the {3(n+1)+1}-th acquired unilluminated image by using a constant velocity model expressed by the following Formulae (9) and (10).

$$X_{3(n+1)} = X_{3n+2} + \tfrac{1}{2}(X_{3n+2} - X_{3n}) \quad (9)$$

$$X_{3(n+1)+1} = X_{3n+2} + (X_{3n+2} - X_{3n}) \quad (10)$$

By estimating the two corneal reflection positions, the calculation unit 22 generates the difference bright pupil image by performing the position correction on the 3(n+1)- th acquired bright pupil image and the {3(n+1)+1}-th acquired unilluminated image.

Furthermore, by obtaining the corneal reflection position $X_{3(n+1)}$, the calculation unit 22 can estimate the corneal reflection position $X_{3(n+1)+2}$ in the {3(n+1)+2}-th acquired dark pupil image by using the following Formula (11).

$$X_{3(n+1)+2} = X_{(3n+1)} + 2(X_{3(n+1)} - X_{3n+2}) \quad (11)$$

As a result, since the two corneal reflection positions $X_{3(n+1)+1}$ and $X_{3(n+1)+2}$ can be obtained, the calculation unit 22 generates the difference dark pupil image by performing the position correction on the {3(n+1)+1}-th acquired unilluminated image and the {3(n+1)+2}-th acquired dark pupil image. Then, the calculation unit 22 generates the difference image by performing the position correction on the difference bright pupil image and the difference dark pupil image and detects the pupil from the difference image.

The calculation unit 22 can track the pupil by repeating the above processes.

In a case where three images are acquired in one cycle, the image acquisition interval may not be constant for the same reason as in the first embodiment. In this case, as in the first embodiment, the calculation unit 22 estimates the corneal reflection position by using a constant velocity model considering the image acquisition interval. Also, as in the first embodiment, there is a case where the interval can be represented by the number of frames.

It is assumed that the time interval from the acquisition of the 3n-th bright pupil image to the acquisition of the (3n+1)-th unilluminated image is $\Delta t_1''$, the time interval from the acquisition of the unilluminated image to the acquisition of the (3n+2)-th dark pupil image is $\Delta t_2''$, and the time interval from the acquisition of the dark pupil image to the acquisition of the 3(n+1)-th bright pupil image is $\Delta t_3''$. As in the first embodiment, the time interval may be a difference between exposure start times, may be a difference between exposure end times, may be a difference between image transmission start times or image transmission end times, or may be expressed based on the number of missing images.

The calculation unit 22 estimates the corneal reflection positions $X_{3(n+1)}$, $X_{3(n+1)+1}$, and $X_{3(n+1)+2}$ by using the following Formulae (12) to (14) corresponding to Formulae (9) to (11). Therefore, even when the image acquisition interval is various, the calculation unit 22 can generate the difference bright pupil image and the difference dark pupil image, from which false corneal reflection is removed, and can generate the difference image from the two images and detect the pupil.

[Math. 5]

$$X_{3(n+1)} = X_{3n+2} + \frac{\Delta t_3^n}{\Delta t_1^n + \Delta t_2^n}(X_{3n+2} - X_{3n}) \quad (12)$$

[Math. 6]

$$X_{3(n+1)+1} = X_{3n+2} + \frac{\Delta t_3^n + \Delta t_1^{n+1}}{\Delta t_1^n + \Delta t_2^n}(X_{3n+2} - X_{3n}) \quad (13)$$

[Math. 7]

$$X_{3(n+1)+2} = X_{3(n+1)} + \frac{\Delta t_1^{n+1} + \Delta t_2^{n+1}}{\Delta t_3^n}(X_{3(n+1)} - X_{3n+2}) \quad (14)$$

The image acquisition unit 21 may acquire the pupil images in the order of "dark pupil image->unilluminated image->bright pupil image" in one cycle. Even in this case, the calculation unit 22 can estimate the corneal reflection position in each of the unilluminated image, the bright pupil image, and the dark pupil image by the same method as described above.

[Third Embodiment]

In the first and second embodiments, the constant velocity model has been applied to the coordinates on the image, that is, the two-dimensional coordinates, but the calculation unit 22 may apply the constant velocity model on three-dimensional coordinates. By estimating the corneal reflection position by applying the constant velocity model on the three-dimensional coordinates, the corneal reflection position can be accurately estimated even when the pupil moves in a direction crossing an imaging plane.

Figure 11:
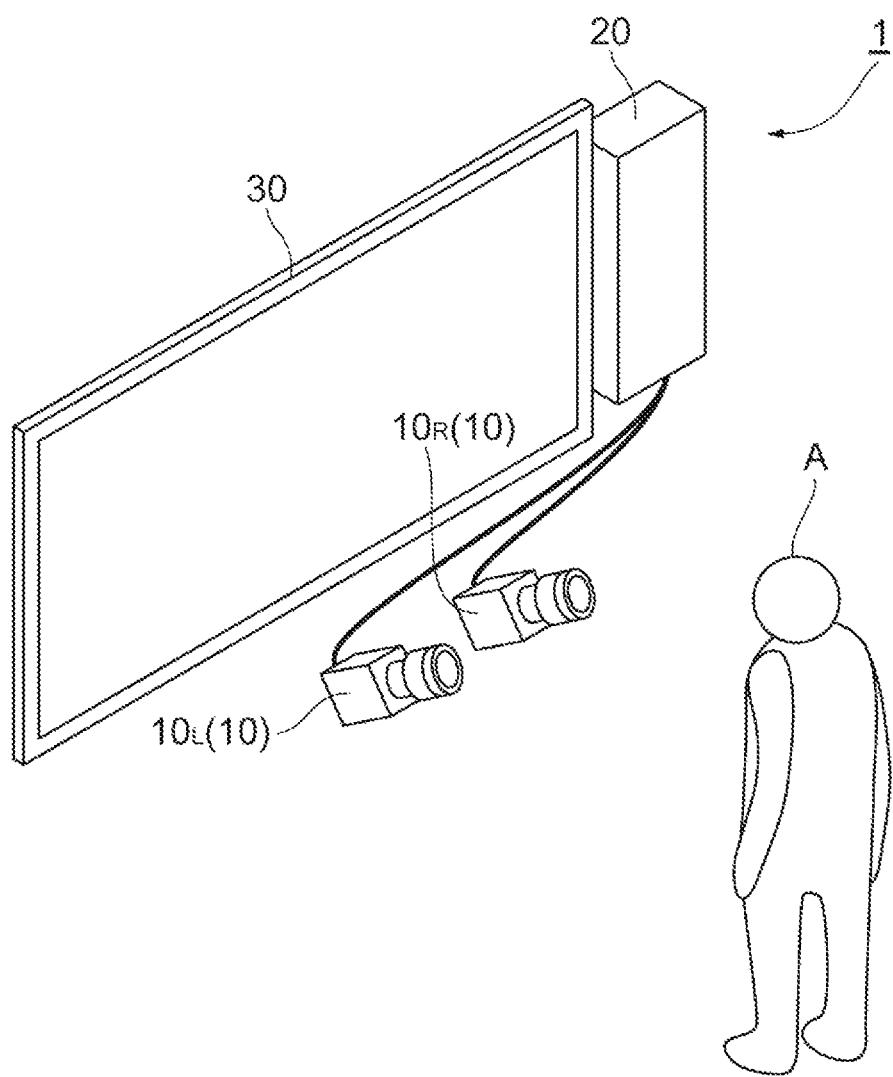
FIG. 11 is a perspective view illustrating a detection system according to a third embodiment.

However, in the case of using the three-dimensional coordinates, the detection system 1 needs to include two cameras 10 functioning as a stereo camera. As illustrated in FIG. 11, a pair of cameras 10 includes a left camera $10_L$ located on the left of the subject A and a right camera $10_R$ located on the subject A. The pair of cameras 10 is disposed at a predetermined interval along a horizontal direction.

In the case of using the pair of cameras 10, the image acquisition unit 21 slightly shifts an operation timing between the two cameras 10, and the exposure time of each individual camera 10 is set to be equal to or shorter than the shift time. The image acquisition unit 21 prevents light from the light source 13 of one camera 10 from affecting the image of the other camera 10 (prevents crosstalk from occurring) by alternately turning on the corresponding light-emitting element 13a and light-emitting element 13b during the exposure time of each camera 10. Then, the image acquisition unit 21 acquires the pupil image from each of the left camera $10_L$ and the right camera $10_R$.

The calculation unit 22 obtains the corneal reflection position on the pupil image from each of the camera $10_L$ and $10_R$ in a certain phase by the methods of the first and second embodiments. The corneal reflection position obtained at this time is two-dimensional coordinates, and the calculation unit 22 obtains three-dimensional coordinates from the two-dimensional coordinates by using a stereo method (stereo matching). The stereo method is a method of previously measuring internal parameters, such as a focal length of a camera lens, a center of an image, and a pixel size, and external parameters, such as a position and attitude of the camera and, when a subject is photographed by a plurality of stereo cameras, determining a spatial position of a point of the image by using the internal parameters and the external parameters based on the coordinates of the point. The internal parameters and the external parameters necessary for the calculation of the three-dimensional coordinates are previously obtained as calibration data and are stored in the calculation unit 22. The method itself of obtaining the three-dimensional coordinates by using the stereo method is a known technique and is also introduced in, for example, the following Reference Documents 1 and 2.

(Reference Document 1) WO 2012/077713
(Reference Document 2) WO 2012/020760

The calculation unit 22 obtains relational expressions of the corneal reflection position in the image coordinate system detected based on output data from the two cameras 10 and the corneal reflection position in the world coordinate system with reference to the calibration data. Next, the calculation unit 22 obtains three-dimensional coordinates of the corneal reflection position in the world coordinate system from the two relational expressions. The calculation unit 22 can obtain three-dimensional coordinates of the corneal reflection position of each of the left and right pupils of the subject A. Subsequently, for each eye, the calculation unit 22 sets, as three-dimensional coordinates of a corneal sphere center, three-dimensional coordinates of an intersection point of a straight line passing through a lens center of the left camera 10$_L$ (points other than the lens center may also be possible) and a corneal reflection point corresponding to the left camera 10$_L$ and a straight line passing through a lens center of the right camera 10$_R$ (points other than the lens center may also be possible) and a corneal reflection point corresponding to the right camera 10$_R$.

On the assumption that the three-dimensional coordinates of the corneal sphere center are obtained in this manner, the method of estimating the corneal reflection position in the case of the process of acquiring four images (bright pupil image->unilluminated image->dark pupil image->unilluminated image) in one cycle as illustrated in FIG. 6 will be described.

The calculation unit 22 performs the process of detecting the corneal reflection from the difference bright pupil image acquired from the 4n-th image (bright pupil image) and the (4n+1)-th image (unilluminated image) with respect to each of the image from the left camera 10$_L$ and the image from the right camera 10$_R$. Subsequently, the calculation unit 22 obtains the coordinates $X'_{4n}$ of the corneal sphere center corresponding to the bright pupil image by using the stereo method as described above. Furthermore, the calculation unit 22 performs the process of detecting the corneal reflection from the difference dark pupil image acquired from the (4n+2)-th image (dark pupil image) and the (4n+1)-th image (unilluminated image) with respect to each of the image from the left camera 10$_L$ and the image from the right camera 10$_R$. Then, the calculation unit 22 obtains the coordinates $X'_{4n+2}$ of the corneal sphere center corresponding to the dark pupil image by using the stereo method. As described above, the coordinates of the corneal sphere center are three-dimensional coordinates. The calculation unit 22 estimates the coordinates $X'_{4n+3}$ of the corneal sphere center in the (4n+3)-th image (unillustrated image) by using a constant velocity model represented by the following Formula (15) based on the coordinates of the two spherical centers.

$$X'_{4n+3} = X'_{4n+2} + \tfrac{1}{2}(X'_{4n+2} - X'_{4n}) \tag{15}$$

In Formula (15), $(X'_{4n+2} - X'_{4n})$ is a movement vector indicating the movement of the corneal sphere center in a three-dimensional sphere. The "movement vector" in the present embodiment is a vector indicating the direction and amount of the movement of the position of the corneal sphere center. Also, in the present embodiment, a reference position used for calculating the movement vector is the position of the corneal sphere center.

Subsequently, the calculation unit 22 converts the estimated coordinates $X'_{4n+3}$ of the corneal sphere center into two-dimensional coordinates on the imaging plane (pupil image). It can be said that the conversion is a process of projecting the three-dimensional coordinates on the imaging plane by using a pinhole model. The two-dimensional position $X_{4n+3}$ on the imaging plane corresponding to the three-dimensional coordinates $X'_{4n+3}(x, y, z)$ may be obtained from the following Formula (16) by using the focal length f of the camera.

$$X_{4n+3} = (x(f/z), y(f/z)) \tag{16}$$

The calculation unit 22 performs conversion into the two-dimensional coordinates with respect to each of the image acquired from the left camera 10$_L$ and the image acquired from the right camera 10$_R$.

Similarly, the calculation unit 22 estimates coordinates $X'_{4(n+1)}$ of the corneal sphere center in the {4(n+1)}-th image, that is, the next bright pupil image, by using a constant velocity model expressed by the following Formula (17).

$$X'_{4(n+1)} = X'_{4n+2} + (X'_{4n+2} - X'_{4n}) \tag{17}$$

Then, the calculation unit 22 converts the estimated coordinates $X'_{4(n+1)}$ of the corneal sphere center into two-dimensional coordinates $X_{4(n+1)}$ by Formula (16).

When the corneal reflection position $X_{4n+3}$ is estimated as described above, the calculation unit 22 generates the difference dark pupil image by performing position correction on the (4n+2)-th image (dark pupil image) and the (4n+3)-th image (unilluminated image) and detects the corneal reflection from the difference dark pupil image. Furthermore, when the corneal reflection position $X_{4(n+1)}$ is estimated, the calculation unit 22 generates the difference bright pupil image by performing position correction on the (4n+3)-th image (unilluminated image) and the {(4(n+1)}-th image (bright pupil image) and detects the corneal reflection from the difference bright pupil image. Then, the calculation unit 22 generates the difference image by performing position correction on the difference dark pupil image and the difference bright pupil image, detects the pupil from the difference image, and obtains an accurate corneal reflection position $X_{4(n+1)}$.

As a result, in each of the image acquired from the left camera 10$_L$ and the image acquired from the right camera 10$_R$, the corneal reflection position $X_{4n+2}$ in the (4n+2)-th image (dark pupil image) and the corneal reflection position $X_{4(n+1)}$ in the {4(n+1)}-th image (bright pupil image) are obtained. Therefore, the calculation unit 22 can estimate the coordinates $X_{4'(n+1)+1}$ of the corneal sphere center in the {4(n+1)+1}-th image (unilluminated image) and the coordinates $X_{4'(n+1)+2}$ of the corneal sphere center in the {4(n+1)+2}-th image (dark pupil image) by using a constant velocity model expressed by the following Formulae (18) and (19).

$$X'_{4(n+1)+} = X'_{4(n+1)} + \tfrac{1}{2}(X'_{4(n+1)} - X'_{4n+2}) \tag{18}$$

$$X'_{4(n+1)+2} = X'_{4(n+1)} + X'_{4(n+1)} - X'_{4n+2}) \tag{19}$$

Then, the calculation unit 22 converts the estimated coordinates $X'_{4(n+1)+1}$ and $X'_{4(n+1)+2}$ of the corneal sphere centers into two-dimensional coordinates $X_{4(n+1)+1}$ and $X_{4(n+1)+2}$ on the imaging plane (pupil image) by Formula (16).

When the corneal reflection position $X_{4(n+1)+1}$ is estimated, the calculation unit 22 generates the difference bright pupil image by performing position correction on the {4(n+1)}-th image (bright pupil image) and the {(4(n+1)+1}-th image (unilluminated image) and detects the corneal reflection from the difference bright pupil image. Furthermore, when the corneal reflection position $X_{4(n+1)+2}$ is estimated, the calculation unit 22 generates the difference dark pupil image by performing position correction on the {4(n+1)+1}-th image (unilluminated image) and the {(4(n+1)+2}-th image (dark pupil image) and detects the corneal reflection from the difference dark pupil image. Then, the calculation unit 22 generates the difference image by performing position correction on the difference bright pupil image and the difference dark pupil image, detects the pupil from the difference image, and obtains an accurate corneal reflection position $X_{4(n+1)+2}$.

The calculation unit 22 can track the pupil by repeating the above processes.

It is obvious that the method of applying the constant velocity model to the coordinates of the corneal sphere center can be applied to the above-described second embodiment in which three images are acquired in one cycle.

[Fourth Embodiment]

In the first embodiment and the second embodiment, the calculation unit 22 estimates the corneal reflection position by using the constant velocity model, but the calculation unit 22 may also perform the estimation by using a constant acceleration model. The calculation unit 22 uses the corneal reflection position in the pupil images (bright pupil images or dark pupil images) acquired one image, two images, and three images before the unilluminated image whose corneal reflection position is to be estimated. Two-dimensional vectors of the corneal reflection positions in a current image, an acquired one image before the current image, an image acquired two images before the current image, and an image acquired three images before the current image are represented by $x_0$, $x_{-1}$, $x_{-2}$, and $x_{-3}$, respectively. Also, the time at which each vector is obtained is represented by $t_0$, $t_{-1}$, $t_{-2}$, and $t_{-3}$, respectively. By doing so, a current velocity $v_0$ is obtained from the coordinates of the current image and the coordinates of the image acquired one image before the current image, a velocity $v_{-1}$ that is one before the current velocity is obtained from the coordinates of the image acquired one image before the current image and the coordinates of the image acquired two images before the current image, and a velocity $v_{-2}$ that is two before the current velocity is obtained from the coordinates of the image acquired two images before the current image and the coordinates of the image acquired three images before the current image. These velocities are obtained by the following Formulae (20) to (22).

$$v_0 = (x_0 - x_{-1})/(t_0 - t_{-1}) \quad (20)$$

$$v_{-1} = (x_{-1} - x_{-2})/(t_{-1} - t_{-2}) \quad (21)$$

$$v_{-2} = (x_{-2} - x_{-3})/(t_{-2} - t_{-3}) \quad (22)$$

Here, $t_0$ to $t_{-3}$ are acquisition time of each image.

From the three velocities, the following two accelerations $a_0$ and $a_{-1}$ are obtained by the following Formulae (23) and (24).

$$a_0 = (v_0 - v_{-1})/(t_0 - t_{-1}) \quad (23)$$

$$a_{-1} = (v_{-1} - v_{-2})/(t_{-1} - t_{-2}) \quad (24)$$

Here, since $a_0 = a_{-1}$ from the constant acceleration model, an unknown value $v_0$ can be obtained from Formulae (23) and (24), and an unknown $x_0$ can be obtained by substituting the calculated $v_0$ into Formula (20).

A case where the constant acceleration model is applied to the example of FIG. 6 will be described. Assuming that an accurate corneal reflection position is obtained in the 4n-th acquired bright pupil image and the (4n+2)-th image (dark pupil image), the times $t_{-3}$, $t_{-2}$, $t_{-1}$, and to correspond to phases $4n$, $4n+2$, $4(n+1)$, and $4(n+1)+1$, respectively. This example corresponds to the estimation of the corneal reflection position in the unilluminated image of the phase $\{4(n+1)+1\}$ and corresponds to Formula (7). Assuming that a velocity in the phase $\{4(n+1)+1\}$ (that is, time to) is represented by $V_{4(n+1)+1}$, Formula (7) is substituted with the following Formulae (25) and (26).

[Math. 8]

$$X_{4(n+1)+1} = X_{4(n+1)} + \frac{\Delta t_1^{n+1}}{\Delta t_3^n + \Delta t_4^n} v_{4(n+1)+1} \quad (25)$$

[Math. 9]

$$v_{4(n+1)+1} = v_{4(n+1)} + \frac{\Delta t_1^{n+1}}{\Delta t_3^n + \Delta t_4^n}(v_{4(n+1)} - v_{4n+2}) \quad (26)$$

where, $v_{4(n+1)} = X_{4(n+1)} - X_{4n+2}$ $v_{4n+2} = X_{4n+2} - X_{4n}$

If up to four consecutive images acquired before the current image are taken into account, the estimation of the corneal reflection position using the constant acceleration model is also possible. The model with an increased order, such as the constant velocity model or the constant acceleration model, is effective when the number of frames per unit time of the camera 10 is large.

It is obvious that the method using the constant velocity model or the constant acceleration model can be applied to the second embodiment in which three images are acquired in one cycle and the third embodiment in which the coordinates of the corneal sphere center are used.

As described above, a corneal reflection position estimation system according to one aspect of the present invention includes: an image acquisition unit configured to continuously acquire an image of an eye of a subject by controlling a camera equipped with a light source, the image acquisition unit being configured to acquire a plurality of pupil images taken by using light from the light source and then acquire one unilluminated image taken without using light from the light source; and an estimation unit configured to calculate positions of corneal reflection or corneal sphere centers, which correspond to the plurality of pupil images, as reference positions, calculate a movement vector of the corneal reflection or the corneal sphere center based on the plurality of reference positions, and estimate the corneal reflection position in the unilluminated image based on at least the movement vector.

A corneal reflection position estimation method according to one aspect of the present invention is a corneal reflection position estimation method, which is performed by a corneal reflection position estimation system including a processor, the corneal reflection position estimation method including: an image acquisition step of continuously acquiring an image of an eye of a subject by controlling a camera equipped with a light source, the image acquisition step including acquiring a plurality of pupil images taken by using light from the light source and then acquiring one unilluminated image taken without using light from the light source; and an estimation step of calculating positions of corneal reflection or corneal sphere centers, which correspond to the plurality of pupil images, as reference positions, calculating a movement vector of the corneal reflection or the corneal sphere center based on the plurality of reference positions, and estimating the corneal reflection position in the unilluminated image based on the movement vector.

A corneal reflection position estimation program according to one aspect of the present invention causes a computer to function as: an image acquisition unit configured to continuously acquire an image of an eye of a subject by controlling a camera equipped with a light source, the image acquisition unit being configured to acquire a plurality of pupil images taken by using light from the light source and then acquire one unilluminated image taken without using light from the light source; and an estimation unit configured to calculate positions of corneal reflection or corneal sphere centers, which correspond to the plurality of pupil images, as reference positions, calculate a movement vector of the corneal reflection or the corneal sphere center based on the plurality of reference positions, and estimate the corneal reflection position in the unilluminated image based on at least the movement vector.

In this aspect, the plurality of reference positions (positions of corneal reflection or corneal sphere centers) corresponding to the plurality of pupil images acquired before the unilluminated image is calculated. Since the pupil image is taken by using light from the light source, the position of the corneal reflection or the corneal sphere center can be obtained from the pupil image. Then, since the movement of the corneal reflection or the corneal sphere center immediately before the acquisition of the unilluminated image can be grasped by obtaining the movement vector of the corneal reflection or the corneal sphere center from the plurality of reference positions, the corneal reflection position of the time point when the unilluminated image was acquired can be estimated from the movement.

If a high-speed camera having a high frame rate (for example, 2,000 fps) is used, a time difference of image acquisition is only 0.5 ms, and the acquisition time of the bright pupil image, the unilluminated image, and the dark pupil image is only 1.5 ms. If the photographing time interval is at this degree, the pupil movement between the images can be ignored even when the head moves during the photographing time interval. However, the high-speed camera is expensive at present and is difficult to simply adopt. On the contrary, since the camera having a frame rate of 240 fps, which is used in the present embodiment, is inexpensive as compared to the high-speed camera, it is easy to introduce into a system, but the time of 4.2 ms described above is not a level that does not require position correction. Therefore, as described in the present embodiment, the position correction of the bright pupil image or the dark pupil image and the unilluminated image can be performed by estimating the corneal reflection position of the time point when the unilluminated image was acquired.

Also, by estimating the corneal reflection position of the unilluminated image, when the position correction of the bright pupil image or the dark pupil image and the unilluminated image is performed, it is possible to detect the pupil while tracking only the window including the corneal reflection position in the image. Therefore, the load of the image processing can be reduced as a whole.

In a case where the corneal reflection position is used as the reference position, the corneal reflection position of the unilluminated image can be easily estimated without considering three-dimensional coordinates or using the stereo method. On the other hand, in a case where the position of the corneal sphere center is used as the reference position, the corneal reflection position of the unilluminated image can be more accurately estimated.

In a corneal reflection position estimation system according to another aspect, an estimation unit can estimate a corneal reflection position in an unilluminated image based on a movement vector and each individual time interval when an image acquisition unit acquires each individual image. The movement of the corneal reflection can be accurately estimated in consideration of the image acquisition time as well as the movement vector.

In a corneal reflection position estimation system according to another aspect, the plurality of pupil images are two pupil images and an estimation unit may calculate reference positions in the two pupil images, calculate a movement vector based on the two reference positions, and estimate a corneal reflection position in an unilluminated image based on at least the movement vector by using a constant velocity model. By using the constant velocity model, it is possible to easily estimate the corneal reflection position in the unilluminated image by using only the two pupil images previously acquired.

In the corneal reflection position estimation system according to another aspect, the plurality of pupil images are three pupil images and an estimation unit may calculate reference positions in the three pupil images, calculate two movement vectors based on the three reference positions, and estimate a corneal reflection position in an unilluminated image based on at least the two movement vectors by using a constant acceleration model. Since the appearance of the movement of the movement vector can be estimated in detail by using the constant acceleration model, it is possible to accurately estimate the corneal reflection position in the unilluminated image.

In a corneal reflection position estimation system according to another aspect, an image acquisition unit may acquire an unilluminated image and then acquire one additional pupil image taken by using light from a light source, and the estimation unit may estimate a corneal reflection position in the additional pupil image based on at least a movement vector. In this case, it is possible to estimate not only the corneal reflection position in the unilluminated image but also the corneal reflection position in the subsequent pupil image.

A pupil detection system according to one aspect of the present invention includes a pupil calculation unit configured to calculate a pupil position based on the corneal reflection position in the unilluminated image, which is estimated by the corneal reflection position estimation system, wherein the plurality of pupil images include one of a bright pupil image and a dark pupil image, the additional pupil image is the other of the bright pupil image and the dark pupil image, and the pupil calculation unit performs a generation of a difference bright pupil image from the bright pupil image and the unilluminated image and a generation of a difference dark pupil image from the dark pupil image and the unilluminated image based on the corneal reflection position in the unilluminated image, generates a difference image from the difference bright pupil image and the difference dark pupil image, and calculates a pupil position based on the difference image.

A pupil detection method, which is performed by a computer system including a processor, the pupil detection method including: a pupil calculation step of calculating a pupil position based on the corneal reflection position in the unilluminated image, which is estimated by the corneal reflection position estimation method, wherein, in the image acquisition step, after the unilluminated image is acquired, one additional pupil image taken by using light from the light source is acquired; in the estimation step, the corneal reflection position in the additional corneal image is estimated based on at least the movement vector; the pupil image acquired immediately before the unilluminated image among the plurality of pupil images includes one of the bright pupil image and the dark pupil image, and the additional pupil image is the other of the bright pupil image and the dark pupil image; and in the pupil calculation step, a generation of a difference bright pupil image from the bright pupil image and the unilluminated image and a generation of a difference dark pupil image from the dark pupil image and the unilluminated image are performed based on the corneal reflection position in the unilluminated image, a difference image is generated from the difference bright pupil image and the difference dark pupil image, and a pupil position is generated based on the difference image.

A pupil detection program according to one aspect of the present invention causes a computer to function as the pupil detection system.

In this aspect, since the corneal reflection position in the unilluminated image is also estimated, the difference bright pupil image and the difference dark pupil image with high accuracy can be generated from the bright pupil image, the unilluminated image, and the dark pupil image continuously taken. Therefore, since the difference image acquired from the difference bright pupil image and the difference dark pupil image are also acquired with high accuracy, an accurate pupil position can be obtained from the difference image.

The present invention has been described in detail based on the embodiments. However, the present invention is not limited to the above embodiments. The present invention can be variously modified without departing from the gist thereof.

(Detection of Gaze)

The calculation unit 22 may detect the gaze from the relative positional relationship of the coordinates of the pupil center and the corneal reflection position obtained by the above-described method. In this case, the detection system 1 also functions as a gaze detection system. A method for strictly performing the gaze detection is disclosed in, for example, Reference Documents 1 and 2 above or Reference Document 3 below.

(Reference Document 3) JP 2005-185431 A

A gaze detection program can be created by adding a module for realizing such a gaze detection function to the detection program P1.

That is, a gaze detection system according to one aspect of the present invention detects a gaze based on the pupil position calculated by the pupil detection system.

A gaze detection method according to one aspect of the present invention detects a gaze based on the pupil position calculated by the pupil detection method.

A gaze detection program according to one aspect of the present invention causes a computer to function as the gaze detection system.

In this aspect, the gaze of the subject can be correctly specified based on the pupil position calculated with high accuracy.

(Detection of Face Orientation)

The calculation unit 22 may detect a face orientation by using the coordinates of the pupil center obtained by the above-described method. In this case, the detection system 1 also functions as a face orientation detection system. A face orientation detection method itself is disclosed in, for example, Reference Document 4 below.

(Reference Document 4) JP 2007-271554 A

According to the method disclosed in Reference Document 4, the calculation unit 22 estimates the corneal reflection position with respect to each of the left and right pupils based on any one of the above embodiments, detects the pupil based on the estimation result, and obtains coordinates of the pupil center. Also, the calculation unit 22 obtains two-dimensional coordinates of left and right nostril centers with reference to the bright pupil image or the dark pupil image. Then, the calculation unit 22 calculates three-dimensional coordinates of the left and right pupil centers and three-dimensional coordinates of the left and right nostril centers based on the two-dimensional coordinates of the left and right pupil centers and the left and right nostril centers, and obtains the face orientation of the subject A (center and face-direction vector). As such, the method of each of the above embodiments can be applied to the calculation of the coordinates of the pupil center which is disclosed in Reference Document 4.

A face orientation detection program can be created by adding a module for realizing such a face orientation detection function to the detection program P1.

That is, a face orientation detection system according to one aspect of the present invention detects a face orientation based on the pupil position calculated by the pupil detection system and the nostril position calculated with reference to the bright pupil image or the dark pupil image.

Also, a face orientation detection method according to one aspect of the present invention detects a face orientation based on the pupil position calculated by the pupil detection method and the nostril position calculated with reference to the bright pupil image or the dark pupil image.

Also, a face orientation detection program according to one aspect of the present invention causes a computer to function as the face orientation detection system.

In this aspect, the face orientation of the subject can be correctly detected based on the pupil position calculated with high accuracy.

(Processing in Case of Failing to Track Pupil)

In a case where the subject A closes his or her eyes during the tracking of the pupil, the pupil and the corneal reflection do not appear in the image. Thus, the calculation unit 22 cannot detect the pupil and fails to track the pupil. In this case, the calculation unit 22 generates a difference image from a pair of a bright pupil image and a dark pupil image without using an unilluminated image and without performing the position correction on that pair, and attempts to detect the pupil from the difference image. The calculation unit 22 repeats the attempt until the pupil detection is successful. Then, once the pupil detection succeeds, the processing of any one of the above embodiments, that is, the pupil detection including the corneal reflection position estimation using the unilluminated image is resumed.

That is, in a pupil detection system according to another aspect, when the calculation of the pupil position based on the corneal reflection position in the unilluminated image is failed, a pupil calculation unit may generate a new difference image from a newly acquired bright pupil image and a newly acquired dark pupil image, without using the unilluminated image, and may calculate the pupil position based on the new difference image, and when the pupil position is obtained based on the new difference image, processing by an image acquisition unit and an estimation unit may be performed and the pupil calculation unit may calculate a corneal position based on a corneal reflection position in a new unilluminated image estimated based on the processing.

In this case, when the calculation of the pupil position using the unilluminated image is failed, a difference image is generated from only the bright pupil image and the dark pupil image to detect the pupil, and when the detection succeeds, the pupil is detected again by using the unilluminated image. Therefore, even after the pupil detection using the unilluminated image is failed because the subject A closes his or her eyes for a moment, it is possible to continuously track the pupil of the subject A.

(Others)

When a Kalman filter is used instead of the constant velocity model, a linear Kalman filter may be used, and when a Kalman filter is used instead of the constant acceleration model, an extended Kalman filter may be used.

Therefore, in the corneal reflection position estimation system according to another aspect, a plurality of pupil images are two pupil images and an estimation unit may calculate reference positions in two pupil images, calculate a movement vector based on the two reference positions, and estimate a corneal reflection position in an unilluminated image based on at least the movement vector by using a constant velocity model or a linear Kalman filter.

Also, in a corneal reflection position estimation system according to another aspect, the plurality of pupil images are three pupil images and an estimation unit may calculate reference positions in the three pupil images, calculate two movement vectors based on the three reference positions, and estimate a corneal reflection position in an unilluminated image based on at least the two movement vectors by using a constant acceleration model or an extended Kalman filter.

The image processing device 20 may acquire two images in one cycle as illustrated in FIG. 12. The (a) of FIG. 12 illustrates an aspect of acquiring a bright pupil image and an unilluminated image in one cycle, and the (b) of FIG. 12 illustrates an aspect of acquiring a dark pupil image and an unilluminated image in one cycle. The image processing device 20 may alternately acquire the bright pupil image (or the dark pupil image) and the unilluminated image and estimate the corneal reflection position in the unilluminated image by applying the methods of the above embodiments.

REFERENCE SIGNS LIST 1 detection system
10 camera
20 image processing device
21 image acquisition unit
22 calculation unit (estimation unit, pupil calculation unit)
P1 detection program
P10 main module
P11 image acquisition module
P12 calculation module

The invention claimed is:

1. A pupil detection system comprising:
at least one memory operable to store program instructions; and
at least one processor operable to access the at least one memory and read and carry out the program instructions, the program instructions including:
image acquisition instructions to cause the at least one processor to continuously acquire an image of an eye of a subject by controlling a camera equipped with a light source which has a first light-emitting element emitting first light with a first wavelength of first transmittance and a second light-emitting element emitting second light with a second wavelength of second transmittance that is less than the first transmittance, wherein the image acquisition instructions cause the at least one processor to acquire a plurality of pupil images taken by using light from the light source and then acquire one unilluminated image taken without using light from the light source, and wherein each of the plurality of pupil images is an image selected from a group consisting of a bright pupil image taken with the first light-emitting element turned on and a dark pupil image taken with the second light-emitting element turned on, the unilluminated image being taken with both the first and second light-emitting elements turned off; and
estimation instructions to cause the at least one processor to calculate positions of corneal reflection or corneal sphere centers, which correspond to each of the plurality of pupil images, as reference positions, calculate a movement vector of the corneal reflection or the corneal sphere center based on a plurality of the reference positions, and estimate the corneal reflection position in the unilluminated image based on at least the movement vector,
wherein, after the unilluminated image is acquired, the image acquisition instructions further comprise instructions to cause the at least one processor to acquire one additional pupil image taken by using light from the light source,
the estimation instructions further comprise instructions to cause the at least one processor to estimate a corneal reflection position in the additional pupil image based on at least the movement vector,
the program instructions further include pupil calculation instructions to cause the at least one processor to calculate a pupil position based on the corneal reflection position in the unilluminated image, which is estimated by the estimation instructions,
the additional pupil image is a different type of pupil image from at least one of the plurality of pupil images acquired by the at least one processor, and
the pupil calculation instructions further comprise instructions to cause the one or more processors to perform a generation of a difference bright pupil image from the bright pupil image and the unilluminated image, and a generation of a difference dark pupil image from the dark pupil image and the unilluminated image, based on the corneal reflection position in the unilluminated image, generate a difference image from the difference bright pupil image and the difference dark pupil image, and calculate the pupil position based on the difference image.

2. The pupil detection system according to claim 1, wherein the estimation instructions further comprise instructions to cause the at least one processor to estimate the corneal reflection position in the unilluminated image based on the movement vector and each individual time interval when each individual image is acquired.

3. The pupil detection system according to claim 1, wherein the plurality of pupil images are two pupil images, and
the estimation instructions further comprise instructions to cause the at least one processor to calculate the reference positions each in the two pupil images, calculate the movement vector based on the two reference positions, and estimate the corneal reflection position in the unilluminated image based on at least the movement vector by using a constant velocity model or a linear Kalman filter.

4. The pupil detection system according to claim 1, wherein the plurality of pupil images are three pupil images, and
the estimation instructions further comprise instructions to cause the at least one processor to calculate the reference positions each in the three pupil images, calculate two movement vectors based on the three reference positions, and estimate the corneal reflection position in the unilluminated image based on at least the two movement vectors by using a constant acceleration model or an extended Kalman filter.

5. The pupil detection system according to claim 1, wherein, when the calculation of the pupil position based on the corneal reflection position in the unilluminated image is failed, the pupil calculation instructions further comprise instructions to cause the one or more processors to generate a new difference image from a newly acquired bright pupil image and a newly acquired dark pupil image, without using an unilluminated image, and to calculate the pupil position based on the new difference image, and when the pupil position is obtained based on the new difference image, processing by the image acquisition instructions and the estimation instructions is performed and the pupil calculation instructions further comprise instructions to cause the one or more processors to calculate a pupil position based on a corneal reflection position in a new unilluminated image estimated based on the processing.

6. A gaze detection system configured to detect a gaze based on the pupil position calculated by the pupil detection system according to claim 1.

7. A face orientation detection system configured to detect a face orientation based on the pupil position calculated by the pupil detection system according to claim 1 and a nostril position calculated with reference to the bright pupil image or the dark pupil image.

8. The pupil detection system according to claim 2, wherein the estimation instructions further comprise instructions to cause the at least one processor to calculate the time interval between the acquisition of the pupil image and the acquisition of the unilluminated image.

9. The pupil detection system according to claim 8, wherein the estimation instructions further comprise instructions to cause the at least one processor to calculate a difference between a first exposure start time when the pupil image is acquired and a second exposure start time when the unilluminated image is acquired, as the time interval.

10. The pupil detection system according to claim 8, wherein the estimation instructions further comprise instructions to cause the at least one processor to calculate a difference between a first exposure end time when the pupil image is acquired and a second exposure end time when the unilluminated image is acquired, as the time interval.

11. The pupil detection system according to claim 8, wherein the estimation instructions further comprise instructions to cause the at least one processor to calculate a difference between a first image transmission start time when the pupil image is acquired and a second image transmission start time when the unilluminated image is acquired, as the time interval.

12. The pupil detection system according to claim 8, wherein the estimation instructions further comprise instructions to cause the at least one processor to calculate a difference between a first image transmission end time when the pupil image is acquired and a second image transmission end time when the unilluminated image is acquired, as the time interval.

13. The pupil detection system according to claim 8, wherein the estimation instructions further comprise instructions to cause the at least one processor to calculate a number of frames between the acquisition of the pupil image and the acquisition of the unilluminated image, as the time interval.

* * * * *